United States Patent [19]

Okumura et al.

[11] 4,037,101

[45] July 19, 1977

[54] METHOD AND APPARATUS FOR ANALYZING FINE GRAINED SUBSTANCES

[75] Inventors: Kimio Okumura; Tatsunori Soya; Yosuke Kauchi, all of Kawasaki; Hideyuki Ohi, Akishima, all of Japan

[73] Assignees: Agency of Industrial Science & Technology; Nihon Denshi Kabushiki Kaisha, both of Tokyo, Japan

[21] Appl. No.: 633,233

[22] Filed: Nov. 19, 1975

[30] Foreign Application Priority Data

Nov. 29, 1974 Japan .............................. 49-138059

[51] Int. Cl.² .......................................... G01N 23/04
[52] U.S. Cl. ..................................... 250/310; 250/307
[58] Field of Search ................ 250/310, 306, 274, 307

[56] References Cited

U.S. PATENT DOCUMENTS

| 3,204,095 | 3/1965 | Watanabe | 250/310 |
|---|---|---|---|
| 3,229,087 | 1/1966 | Shapiro | 250/310 |
| 3,479,506 | 11/1969 | Dörfler | 250/310 |
| 3,733,483 | 5/1973 | Green et al. | 250/310 |
| 3,733,484 | 5/1973 | Bayard | 250/310 |
| 3,909,612 | 9/1975 | Gibbard | 250/310 |

Primary Examiner—Alfred E. Smith
Assistant Examiner—B. C. Anderson
Attorney, Agent, or Firm—Webb, Burden, Robinson & Webb

[57] ABSTRACT

A rock specimen is step scanned in an electron probe x-ray microanalyzer. A plurality of x-ray spectrometers (for example three) forming a part of said electron probe x-ray microanalyzer simultaneously detect characteristic x-rays corresponding to three elements at each scanning point on the rock specimen. The concentration of each element is calculated from the output signals of said plurality of x-ray spectrometers and the calculated elemental concentrations are then converted into atomic ratios accordingly. From this information, the type of mineral at each scanning point is designated by a character which is recorded on a display means in synchronism with the step scanning so as to display a mineral map of the specimen being examined.

5 Claims, 4 Drawing Figures

METHOD AND APPARATUS FOR ANALYZING FINE GRAINED SUBSTANCES

This invention relates to the method and apparatus applicable for use in the study of fine grained minerals, zoned minerals, exsolution lamellae, etc. in conjunction with an electron probe x-ray microanalyzer.

An effective method for quantitatively analyzing the abundancy of minerals in rocks is the so called "Modal Analysis" method. In this method, it is necessary to obtain a total square of the grains having the same phase (mineral) within a given area on the surface of a bulk rock specimen. By so doing, the content ratio of the various phases constituting the disproportional bulk rock specimen can be assumed by ascertaining the ratio of the total squares occupied by respective phases. Qualitative analysis of the phase in the grained mineral is carried out with the aid of optical, x-ray, etc. apparatus. For fine (micro) area analysis, an electron probe x-ray microanalyzer is widely used as it enables the concentration distribution of the respective elements on a selected area of the specimen surface to be obtained. However, the concentration of a single element is insufficient to distinguish between one type of phase and another due to the complex texture and chemical complexity of the mineral. Accordingly, it is necessary to obtain the atomic ratio in each grain of the specimen in order to phase analyze the rock specimen. For this purpose, a plural concentration map of the different elements pertaining to the same micro-area of the specimen is measured by the electron probe x-ray microanalyzer, the resultant distribution maps being used for phase analysis. However, phase analysis by this method is extremely time consuming and also lacks sufficient accuracy with regard to the positional adjustment of each distribution map.

One of the main objects of this invention is to determine the kind of mineral constituting a fine grain of the bulk rock specimen quickly and accurately.

Another object of this invention is to obtain the phase distribution of the fine grain on the specimen surface of rock, alloy, etc.

These and other advantages of this invention will become apparent by reading the following description in conjunction with the accompanying drawings of which;

Figure 1:
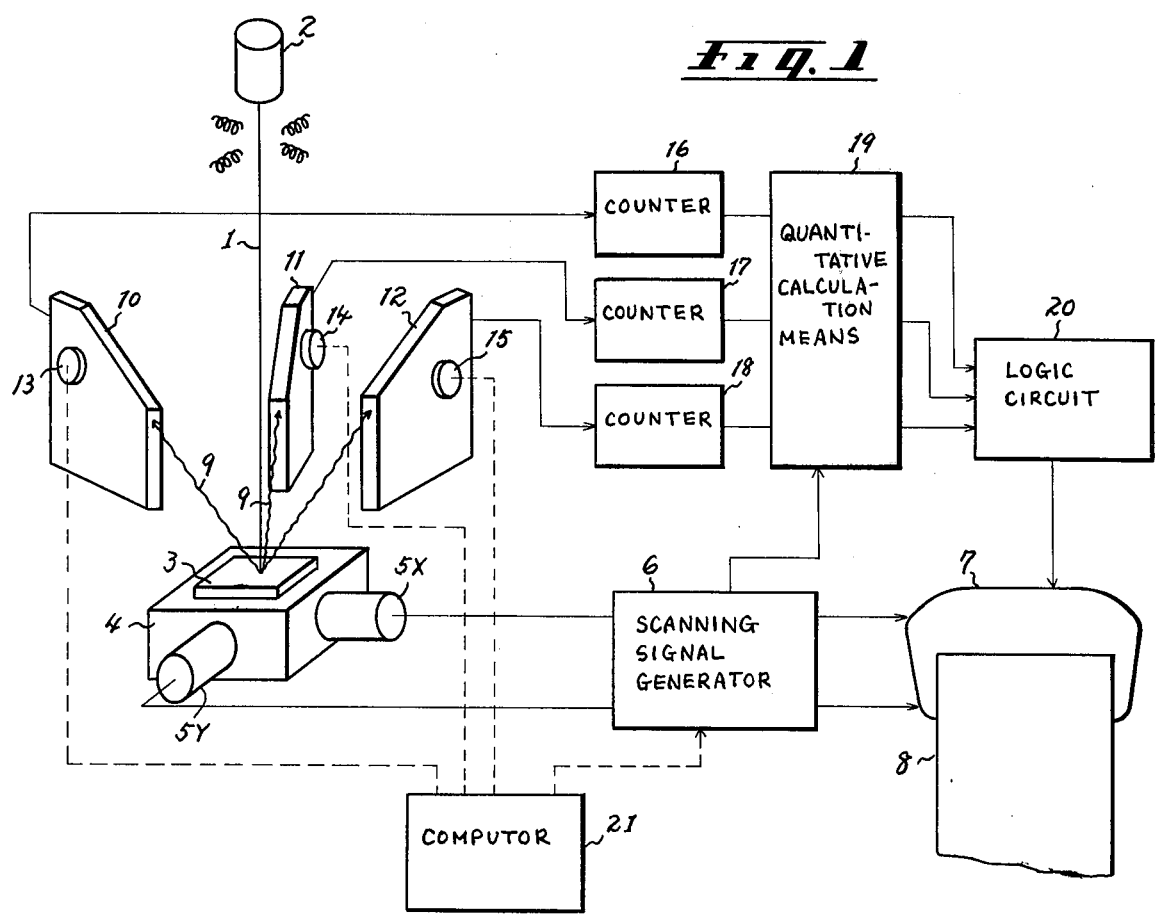
FIG. 1 is a schematic drawing showing one embodiment of this invention.

In FIG. 1, an electron beam 1 generated by an electron gun 2 is focused on a rock specimen 3 by an electron lens system (not shown). The rock specimen 3 is arranged on movable stage 4. The movable stage 4, complete with specimen, is moved digitally in the X and Y direction on a plane perpendicular to the electron beam 1 by means of pulse motors 5X and 5Y which are controlled or driven by signals from a scanning signal generator 6. Alternatively, the electron beam 1 can be scanned over a selected area of the specimen surface by deflection coils. Regardless of the method used, the electron beam spot is digitally scanned over a selected area of the specimen surface. The scanning signal generator 6 has related therewith a character display means 7. Scanning signals from the scanning signal generator are applied to the display means 7. The scanning signals control the position of the typing paper 8 in the character display means 7.

X-rays 9 radiated from the specimen 3 by electron beam irradiation enter wavelength dispersive x-ray spectrometers 10, 11 and 12 where x-rays having characteristic wavelengths are respectively and selectively detected, said detected wavelengths being adjusted by goniometer control means 13, 14 and 15. Accordingly, each spectrometer measures signals corresponding to three different elements (e.g, Ca, Mg and Fe), the respective output signals of which are fed into quantitative calculation means 19 via counters 16, 17 and 18 where the concentration of the three elements is calculated. The calculation is based on output signals $I_1$, $I_2$ and $I_3$ of said counters. The quantitative calculation means 19 also memorizes $I_{01}$, $I_{02}$ and $I_{03}$ which represent the signals from the respective spectrometers attributable to a previously measured standard specimen, the content ratios of the constituent elements of which are known. In this case, the approximate concentration of the three elements is calculated from the ratio $I_1/I_{01}$, etc.

Figure 2:
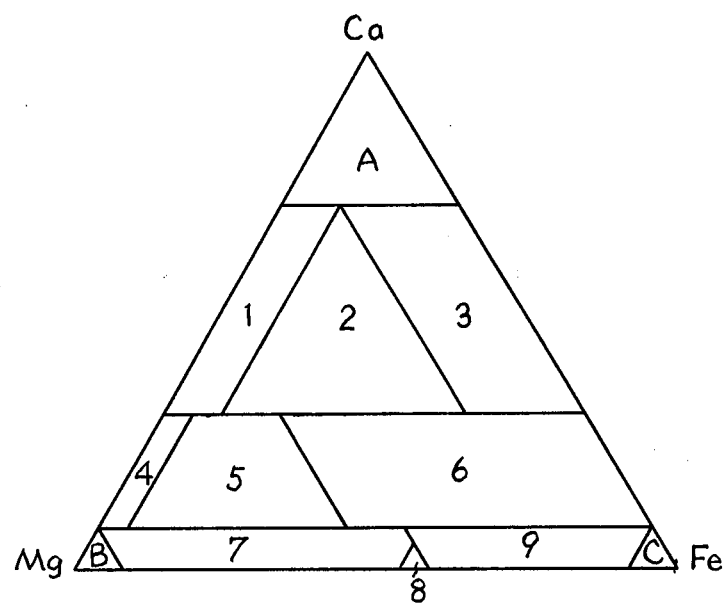
FIG. 2 is a schemtaic phase diagram showing "composition areas" of minerals in a ternary system of the atomic ratio of respective elements.
Figure 3:
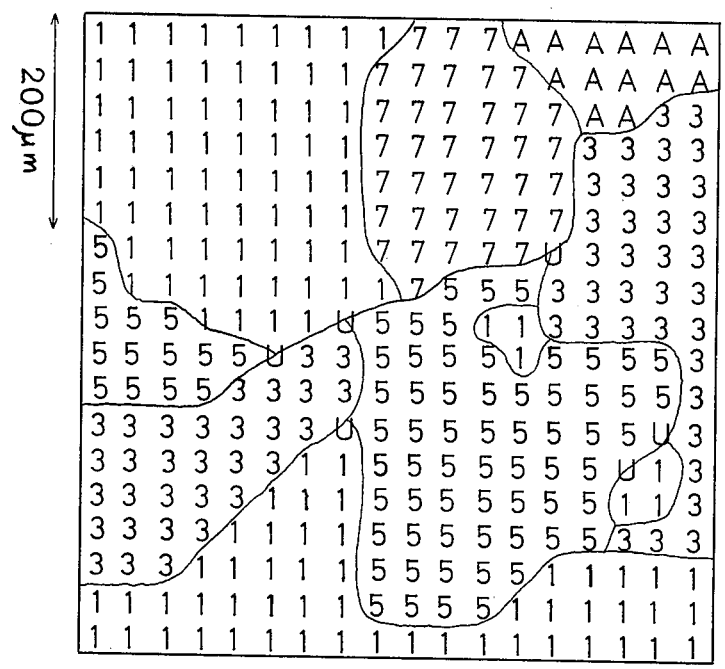
FIG. 3 is a chart showing the fine mineral distribution on the surface of rock obtained by using the embodiment shown in FIG. 1.

The above calculation may take into account various correction factors to improve the accuracy of the quantitative measurement. Thus, the concentration of each element is measured simultaneously during a fixed counting time at each beam irradiating point on the specimen surface. Next, the three concentration signals are applied to a logic circuit 20 in which concentrations in weight percentage are divided by atomic weight and converted into the atomic ratios of three elements. Another function of the logic circuit 20 is to compare each atomic ratio with a memorized "composition area." A character or number corresponding to an appropriate phase or composition area is assigned to the location being stepwise scanned. The composition areas in question are designated in a ternary system according to the atomic ratio of the respective elements in compliance with the mineral. The ternary system of Ca, Mg and Fe, for example, is shown in FIG. 2 where 1, 2, ... 9 represent, Augite, Olivine, Pigeonite, etc. If the atomic ratio of any scanned point on the specimen surface does not belong in any composition area in FIG. 3, the logic circuit 20 designates a character, e.g., "U" to indicate the phase is unidentified. The assigned character output signal of the logic circuit 20 is then fed into the display system so as to type the character on chart paper 8. At the same time, the scanning signal generator 6 supplies a reset signal to the quantitative calculation means 19 in synchronism with the digital step scanning of movable stage 4, and a positioning signal to the character display means 7 so as to designate the type position. After typing the character, the movable stage 4 moves to the next point and the process is repeated until all the step scanning points have been identified. Additionally, the use of a four dimensional system for displaying the composition area is quite effective for decreasing the number of "U"s in the map.

A salient feature of this invention is that measurement accuracy is, to all intents and purposes, unaffected by electron beam current fluctuation which occurs when measurements are carried out over a long period of time.

The computer 21 (FIG. 1) is for controlling spectrometers 10, 11 and 12 and for designating the mapping starting point, the number of counting points and the interval between each analytical point in the generator 6.

Figure 4:
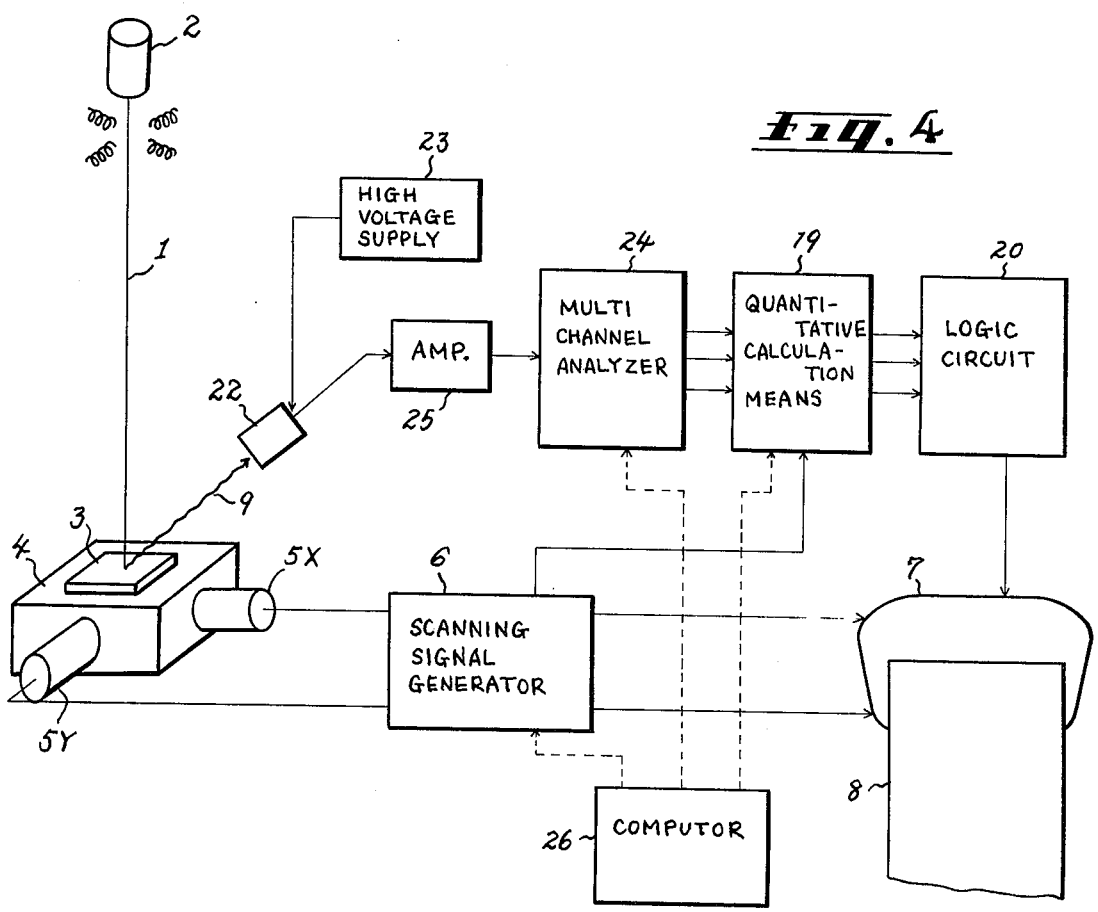
FIG. 4 is a schematic diagram showing another embodiment of this invention.

FIG. 4 shows another embodiment of this invention. This embodiment is different from that shown in FIG. 1 in that an energy dispersive x-ray spectrometer having a solid state detector (SSD) 22 is employed instead of wavelength dispersive x-ray spectrometers 10, 11 and 12. In this embodiment, 23 is a high voltage power supply for the SSD 22, the pulsed output of which is applied to a multi-channel analyzer 24 via an amplifier 25. The output signals of the multi-channel analyzer 24 corresponds respectively to the characteristic x-ray determined by the pulse height of the input signal, said output signals being connected to a quantitative calculation means 19 and logic circuit 20 in the same way as in the embodiment described in FIG. 1. The computer 26 controls the multi-channel analyzer 24, the quantitative calculation means 19 and scanning signal generator 6.

Variations of the above described embodiments are within the scope of this application. For example, a color cathode-ray tube can be used instead of the character display means 7. In this case, the respective colors correspond to a given composition area.

Having thus described our invention with the detail and particularity as required by the patent laws, what is desired protected by Letters Patent is set forth in the following claims.

We claim:

1. In a method of analyzing the fine texture of a specimen comprising the steps for
   a. irradiating the specimen surface with a fine diameter electron beam,
   b. scanning the irradiating position two-dimensionally over a given area on said specimen surface,
   c. measuring the characteristic x-rays produced as a result of beam irradiaton corresponding to certain elements,
   d. calculating the content ratios of each element from the results of said characteristic x-ray measurement, the improvement comprising the steps for
   e. generating signals from the content ratios of said elements which are indicative of the chemical phase at the point being irradiated, and
   f. displaying said signals to-dimensionally in synchronism with said scanning of the irradiating position.

2. In a device for analyzing the fine texture of a specimen substance comprising
   a. an irradiating means for irradiating the specimen surface with an electron beam,
   b. a scanning means for scanning said irradiating position two-dimensionally over a given area on said specimen surface,
   c. an x-ray analyzing means for measuring the characteristic x-rays produced as a result of beam irradiation,
   d. calculating means for calculating the content ratios of each element from the outputs of said x-ray analyzing means,
   the improvement comprising
   e. means for generating signals from the content ratios of said elements which are indicative of the chemical phase at the point being irradiated, and
   f. display means for displaying the signals two-dimensionally in synchronism with said scanning means.

3. A device as claimed in claim 2, in which said x-ray analyzing means is comprised of a plurality of wavelength dispersive x-ray spectrometers.

4. A device as claimed in claim 2, in which said x-ray analyzing means is comprised of an energy dispersive x-ray spectrometer.

5. A device as claimed in claim 2, in which said display means is comprised of a character display means.

* * * * *